(12) United States Patent
Miyazawa et al.

(10) Patent No.: US 8,158,004 B2
(45) Date of Patent: Apr. 17, 2012

(54) METHOD OF MANUFACTURING SUBSTANCES BY SUPERCRITICAL FLUID CHROMATOGRAPHY

(75) Inventors: Kenichiro Miyazawa, Myoko (JP); Takeshi Ishiguro, Myoko (JP)

(73) Assignee: Daicel Chemical Industries, Ltd., Osaka-Shi, Osaka (JP)

( * ) Notice: Subject to any disclaimer, the term of this patent is extended or adjusted under 35 U.S.C. 154(b) by 0 days.

(21) Appl. No.: 13/138,672

(22) PCT Filed: Oct. 22, 2009

(86) PCT No.: PCT/JP2009/068544
§ 371 (c)(1),
(2), (4) Date: Sep. 15, 2011

(87) PCT Pub. No.: WO2010/005122
PCT Pub. Date: Jan. 14, 2010

(65) Prior Publication Data
US 2012/0006750 A1    Jan. 12, 2012

(30) Foreign Application Priority Data
Apr. 2, 2009  (JP) ................. 2009-090398

(51) Int. Cl.
*B01D 15/08* (2006.01)
(52) U.S. Cl. ............... 210/659; 210/656; 210/198.2
(58) Field of Classification Search ......... 210/635, 210/656, 659, 198.2, 634; 95/82, 89; 96/101; 422/70
See application file for complete search history.

(56) References Cited

U.S. PATENT DOCUMENTS

| | | | |
|---|---|---|---|
| 6,576,125 B2 * | 6/2003 | Berger et al. | 210/198.2 |
| 7,678,276 B2 | 3/2010 | Matabe | |
| 2003/0034307 A1 * | 2/2003 | Berger et al. | 210/656 |
| 2006/0266709 A1 * | 11/2006 | Matabe et al. | 210/656 |
| 2011/0000853 A1 * | 1/2011 | Valery et al. | 210/659 |
| 2011/0015418 A1 | 1/2011 | Krumbholz et al. | |

FOREIGN PATENT DOCUMENTS

| | | |
|---|---|---|
| JP | 06-011497 | 1/1994 |
| JP | 07-294503 | 11/1995 |

OTHER PUBLICATIONS

Abstract of WO 2007/147554, Dec. 27, 2007.*
Abstract of EP 1,703,280, Sep. 20, 2006.*
"Foundations of retention in partition chromatography", by C. Poole et al, Journal of Chromatography A, vol. 1216, 2009, pp. 1530-1550.
"Hold-and-flush, a novel fraction collection method in semi-preparative subcritical and supercritical fluid chromatography", by J. Wu et al, Journal of Chromatography A, vol. 1042, 2004, pp. 169-172.
"Gradient Methods in Supercritical Fluid Chromatography", Klesper et al, The Journal of Supercritical Fluids, vol. 1, 1988, pp. 45-69.

* cited by examiner

*Primary Examiner* — Ernest G Therkorn
(74) *Attorney, Agent, or Firm* — Flynn, Thiel, Boutell & Tanis, P.C.

(57) ABSTRACT

Provided is a method of manufacturing target substances with use of supercritical fluid chromatography, by which the following are achieved: solution of a problem at the time of sequential injections of samples containing the target substances; an increase of a treatment amount of separation per unit time; and improvement of efficiency in separation. The method includes the steps of: injecting the sample containing the target substances into a mobile phase; and returning composition of the mobile phase to a pre-change state after changing the composition of the mobile phase. The step of returning the composition of the mobile phase to the pre-change state after changing the composition of the mobile phase is performed during a period of time from detection of a peak of one of the target substances which is eluted latest from a column among the target substances separated by the supercritical fluid chromatography apparatus to injection of the next sample, whereby the problem is solved.

4 Claims, 7 Drawing Sheets

Injection interval can be shorten by 1 min by using THF, and by approximately 2 min by using MeOH.

METHOD OF MANUFACTURING SUBSTANCES BY SUPERCRITICAL FLUID CHROMATOGRAPHY

REFERENCE TO RELATED APPLICATIONS

This application is a 371 of PCT/JP2009/068544 filed Oct. 22, 2011.

TECHNICAL FIELD

The present invention relates to a method of manufacturing substances by supercritical fluid chromatography, and to a supercritical fluid chromatography apparatus.

BACKGROUND ART

In the supercritical fluid chromatography apparatus, a supercritical fluid is used as a mobile phase. The supercritical fluid has higher diffusibility and lower viscosity than those of an ordinary solvent. Therefore, by using the supercritical fluid chromatography apparatus, for example, it is possible to separate at high speed an optical isomer which is difficult to separate.

In such a supercritical fluid chromatography apparatus, a supercritical fluid formed of carbon dioxide or the like is used as the mobile phase, and, after injecting a sample into the mobile phase and dissolving components of the sample in the mobile phase, the components of the sample in the mobile phase are separated by regulating a pressure, a temperature, and the like of the mobile phase. Alternatively, a mobile phase is formed by mixing the supercritical fluid with a solvent such as ethanol referred to as an entrainer or a modifier, and separation is performed by regulating a pressure, a temperature, and the like of the mobile phase.

In Patent Document 1, there is proposed a technology of detecting and washing off components having a large molecular weight and no ultraviolet absorption from a column by providing a second injector on an upstream side of a sample injector and by coupling an output side of a constant pressure release valve with a light diffusion detector.

Further, in Patent Document 2, there is proposed a technology of fractionating and recovering a sample by performing elution while sequentially replacing solvents each having different solvent strength when the sample is eluted from a column in which the sample is absorbed by using a supercritical fluid into which the solvents are added as modifiers. However, in these technologies, examination has not been made in view of improving efficiency in fractionation, particularly of fractionating large amounts of target substances from the sample by sequentially injecting the samples, and thus these technologies are not suitable for industrial mass production.

RELATED ART DOCUMENTS

Patent Documents

Patent Document 1: JP 06-11497 A
Patent Document 2: JP 07-294503 A

SUMMARY OF THE INVENTION

Problem to be Solved by the Invention

Under the circumstance as described above, the inventors of the present invention have devoted themselves to examine a technology by which the samples can be sequentially injected so that industrial mass production is realized. In the course of examining related arts, the inventors of the present invention have focused on the fact that, in column absorption supercritical fluid chromatography, when particularly performing fractionation operation for loading a relatively large amount of chemical compound to be separated, column absorption behavior exhibits nonlinear features, and hence its peak shape extremely differs from a Gaussian line shape and the peak shape having significant tailing is exhibited. The "tailing" described herein represents a graph curve like a long gentle downslope after the peak as shown in FIG. 2. When the samples are injected sequentially in such a circumstance, the samples have to be reinjected after tailing is reduced satisfactorily. When next sample is injected before tailing is reduced satisfactorily, a tailing component is mixed with a peak component of the next-injected sample. Accordingly, purity of the separated chemical compound is decreased. As a result, a treatment amount of separation per unit time has to be decreased.

An object of the present invention is to provide a method of solving the above-mentioned problem at the time of sequential injections, accelerating timing to reinject the sample at the time of sequential injections, increasing the treatment amount of separation per unit time, and improving efficiency in separation.

Means for Solving the Problem

The inventors of the present invention have devoted themselves to examine means for reducing the tailing earlier, and have found out the fact that the reduction of tailing is accelerated by changing the composition of the mobile phase containing the supercritical fluid and the solvent in the column. Thus, the present invention has been completed.

The present invention provides a method of manufacturing target substances by, with use of a supercritical fluid chromatography apparatus, separating the target substances from a sample injected into a mobile phase containing a supercritical fluid and a solvent. The method includes the steps of:

injecting the sample into the mobile phase;

changing composition of the mobile phase after injecting the sample into the mobile phase; and returning the composition of the mobile phase to a pre-change state after changing the composition of the mobile phase, characterized in that the step of changing the composition of the mobile phase and the step of returning the composition of the mobile phase to the pre-change state are performed during a period of time from detection of a peak of one of the target substances which is eluted latest from the column among the target substances separated by the supercritical fluid chromatography apparatus to injection of the next sample.

Effects of the Invention

According to the method of the present invention, in comparison with an ordinary method, reduction of peak tailing occurs earlier, and hence it is possible to accelerate timing to reinject the sample. Therefore, it is possible to increase a treatment amount of the sample per unit time, and to improve separation performance of supercritical fluid chromatography.

MODE FOR CARRYING OUT THE INVENTION

Figure 1:
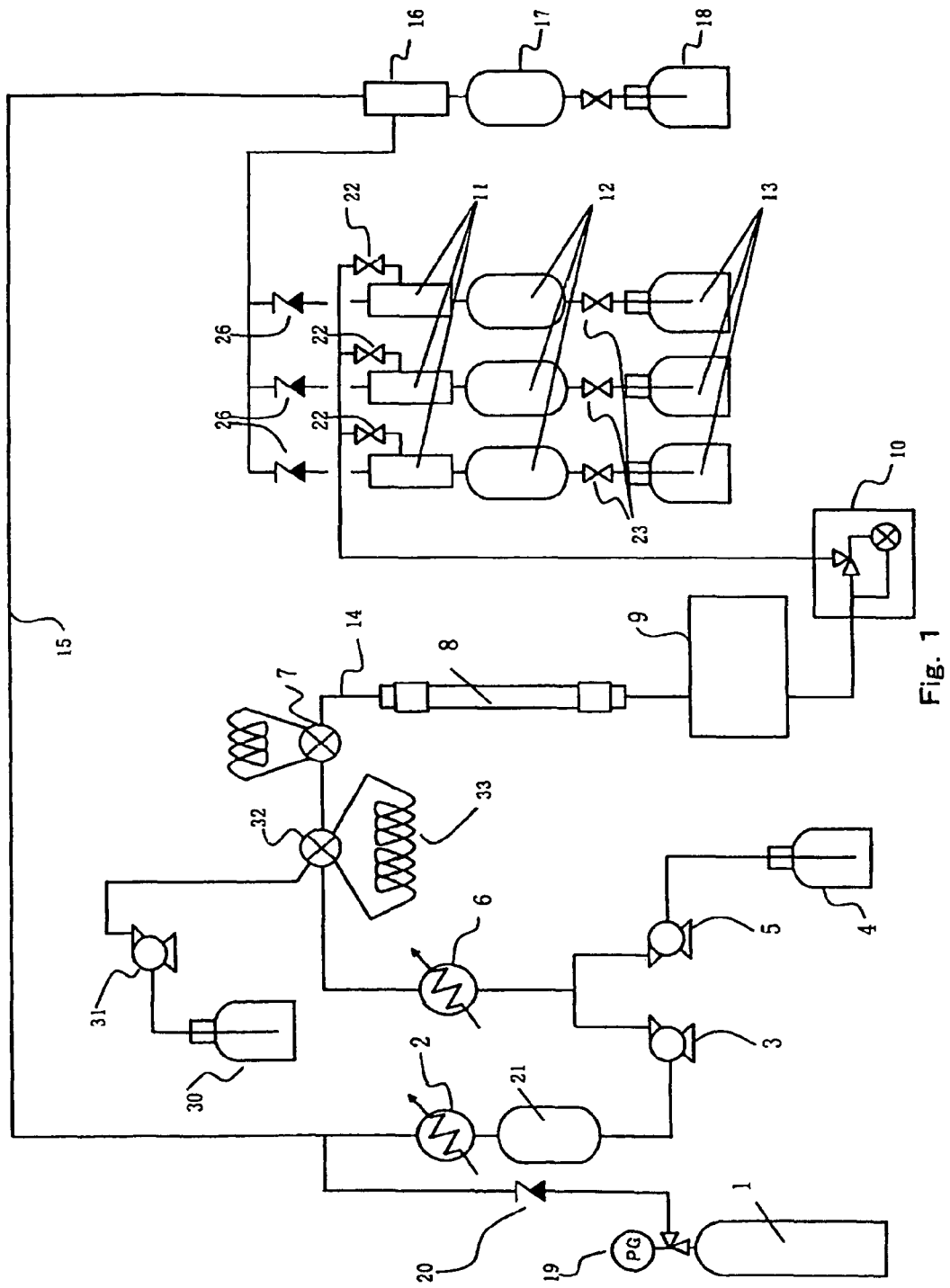
FIG. 1 is a schematic view illustrating an example of a supercritical fluid chromatography apparatus according to the present invention.

A method according to the present invention is applied to a supercritical fluid chromatography apparatus for separating target substances from a sample injected into a mobile phase containing a supercritical fluid and a solvent.

The mobile phase used in the present invention is not particularly limited as long as the mobile phase contains the supercritical fluid and the solvent. The mobile phase can be formed by mixing the supercritical fluid with the solvent, or can be formed by increasing one or both of a pressure and a temperature of a mixed fluid containing a solvent and a liquefied gas used as a raw material for the supercritical fluid. The mobile phase can be formed by using, for example, well-known heat exchanger and high-pressure pump.

The supercritical fluid is a substance having any one or both of a critical pressure or more and a critical temperature or more (that is, substance at a supercritical state). Examples of the substance to be used as the supercritical fluid include carbon dioxide, ammonia, sulfur dioxide, a hydrogen halide, nitrous oxide, hydrogen sulfide, methane, ethane, propane, butane, ethylene, propylene, a halogenated hydrocarbon, and water.

As the solvent, one or two more kinds of solvents are selected among a variety of well-known solvents in accordance with kinds of the target substances, a kind of the supercritical fluid, and the like. Examples of the solvent include lower alcohols such as methanol, ethanol, and 2-propanol, a ketone such as acetone, tetrahydrofuran, acetonitrile, ethyl acetate, and water.

A mixing ratio in the mobile phase between the supercritical fluid and the solvent can be set to a mixing ratio that is ordinarily used for the mobile phase in supercritical fluid chromatography, and can be set to an appropriate mixing ratio by considering the substance to be used as the supercritical fluid and the kind of the solvent. In particular, a mixing ratio ranging from 60:40 to 95:5 is preferred, and a mixing ratio ranging from 80:20 to 95:5 is more preferred.

The above-mentioned supercritical fluid chromatography apparatus is not particularly limited as long as the supercritical fluid chromatography apparatus is capable of separating the target substances from the sample injected into the mobile phase. The above-mentioned supercritical fluid chromatography apparatus can be configured by applying, to an ordinary supercritical fluid chromatography apparatus, a device described below for performing a step of returning composition of the mobile phase to a pre-change state after changing the composition of the mobile phase.

Step of Injecting Sample into Mobile Phase According to the Present Invention

A step of injecting the sample according to the present invention can be performed similarly to operation ordinarily performed in the supercritical fluid chromatography, and can be performed by utilizing a well-known technology. For example, there can be adopted an injecting method causing no fluctuation in pressure at the time of injection as described in JP Hei 05-307026 A. Alternatively, there can be adopted an injecting method allowing to freely regulating a pressure of the sample injected into the mobile phase with a simple configuration as described in JP 2006-58146 A.

Figure 2:
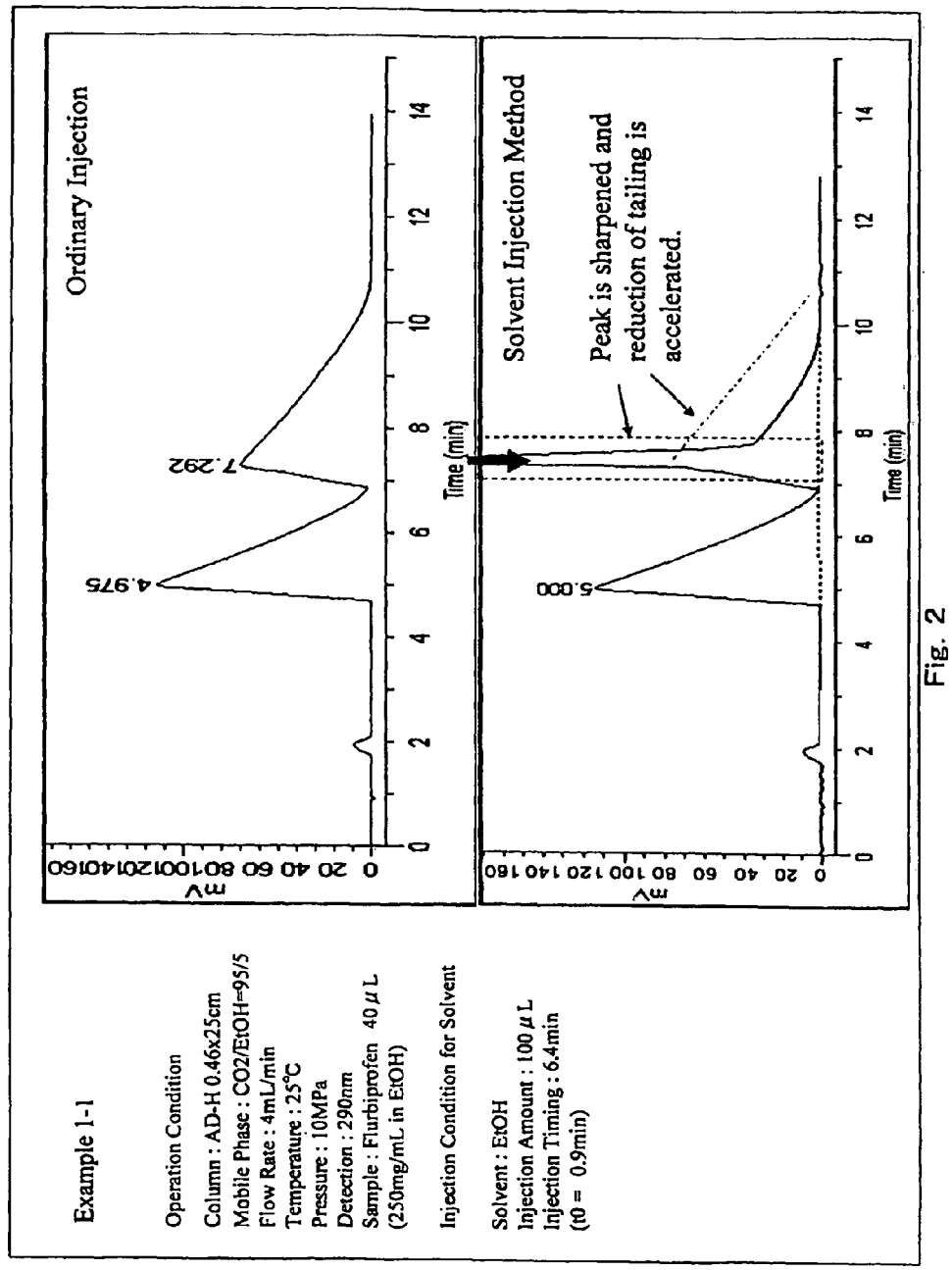
FIG. 2 is a graph showing a reduction of peak tailing according to Example 1.

Step of Changing Composition of Mobile Phase According to the Present Invention and Step of Returning Composition of Mobile Phase to Pre-change State In a step of changing the composition of the mobile phase according to the present invention, the composition of the mobile phase containing the supercritical fluid and the solvent is changed. In the present invention, by changing the composition of the mobile phase in this step, it is possible to accelerate a reduction of tailing of peaks. As described above, in column absorption supercritical fluid chromatography, in a case of particularly performing fractionation operation for loading a relatively large amount of chemical compound to be separated, the peaks exhibit significant tailing as shown in FIG. 2. When next sample is injected before this tailing is reduced, tailing components are mixed with peak components of the next-injected sample. As a result, purity of the separated chemical compound is disadvantageously decreased. Thus, injection of next sample has to be performed after the reduction of tailing is completed. Therefore, by accelerating the reduction of tailing, it is possible to accelerate timing to inject the next sample. In the present invention, by changing the composition of the mobile phase, it is possible to promote extraction of the peak components from a column, and to accelerate the reduction of tailing.

In the present invention, the same effects as those of a step gradient method in liquid chromatography are obtained by changing the composition in the mobile phase, and the reduction of tailing is accelerated by promoting the extraction of the peak components from the column. In the supercritical fluid chromatography, a supercritical fluid having high diffusibility and low viscosity is used, and hence a flow rate of the mobile phase is high and equilibration of the column is rapid. Therefore, even when the composition in the mobile phase is changed, the column is rapidly returned to pre-change environment, and hence it is possible to inject the next sample immediately after the tailing is reduced. As a result, it is possible to increase a treatment amount of sample per unit time, and to improve efficiency and productivity.

A step of changing the composition of the mobile phase according to the present invention may be performed by using any method as long as the step can be performed in the supercritical fluid chromatography apparatus. For example, the composition of the mobile phase can be changed by increasing a solvent ratio in the mobile phase. In the following, a specific method of changing the composition of the mobile phase is described.

As a method of increasing the solvent ratio in the mobile phase, for example, a solvent injecting device for changing the composition of the mobile phase may be provided in the supercritical fluid chromatography apparatus separately from a mobile phase forming device. The solvent is already contained in the mobile phase. However, separately from a device for injecting the solvent into the mobile phase, the solvent injecting device is provided on an upstream side of the column and on a downstream side of the mobile phase forming device, and thus the solvent ratio in the mobile phase can be increased. The solvent injecting device may be, for example, a solvent injecting device including loop piping for keeping the solvent to be injected, a flow passage switching valve, and a solvent injecting pump.

The loop piping used in the solvent injecting device is a pipe having a predetermined capacity. When the loop piping is provided, quantitativeness of injection of the sample is improved, and a larger amount of sample can be preferably injected. In the present invention, the capacity of the loop piping varies depending on conditions such as a kind of the column to be used in the supercritical fluid chromatography apparatus, an inner diameter of the column, the kinds of the target substances, and the composition of the mobile phase. However, it is necessary to inject the large amount of solvent at once. Accordingly, the loop piping of the solvent injecting device is larger in size than loop piping of a sample injecting device, and piping capable of keeping the large amount of solvent is suitable as the loop piping of the solvent injecting device.

The flow passage switching valve used in the solvent injecting device is not particularly limited as long as the flow passage switching valve is a valve or faucet which is provided in a flow passage of the mobile phase and is freely opened and closed. For example, there can be exemplified a valve which performs switching of the flow passage of the mobile phase by using a two-way valve and a butterfly valve in combination, or by using a three-way valve. As the solvent injecting pump used in the solvent injecting device, there can be used a high-pressure pump used for injecting the sample in the supercritical fluid chromatography apparatus.

When the solvent injecting device is used, injection of the solvent is performed by switching the flow passage switching valve and feeding the solvent into the mobile phase in the column with use of the solvent injecting pump. In terms of injection of the solvent, the solvent is preferably injected in a moment by an amount equal to or more than the injecting volume of the sample, preferably equal to or more than two times, more preferably equal to or more than five times the injecting volume of the sample. As the upper limit, the solvent is preferably injected by an amount equal to or less than thirty times, preferably equal to or less than twenty times, more preferably equal to or less than fifteen times the injecting volume of the sample. By setting the injection amount of solvent in this way, the reduction of tailing of the peaks is further accelerated.

Further, a step of returning the composition of the mobile phase to the pre-change state according to the present invention is a step of returning the composition of the mobile phase to a steady state after changing the composition of the mobile phase by the above-mentioned method. This step may be performed by any method as long as this step can be performed in the supercritical fluid chromatography apparatus. When the solvent injecting device is used in particular, the flow passage switching valve is switched, and the flow passage switching valve is returned to its original state after feeding the solvent into the mobile phase in the column by the solvent injecting pump. As a result, switching to the flow passage of the mobile phase from the mobile phase forming device is performed. As described above, in the supercritical fluid chromatography, the flow rate of the mobile phase is high and equilibration of the column is rapid, and hence the composition of the mobile phase is rapidly returned to the pre-change composition by performing switching to the flow passage of the mobile phase. The solvent injecting device can be preferably used because it is possible to easily change the composition of the mobile phase, and to easily return the composition of the mobile phase to the original composition.

Both the step of changing the composition of the mobile phase and the step of returning the composition of the mobile phase to the pre-change state according to the present invention are preferably performed in a moment. It suffices that "a moment" as described herein is a period of time enough for generating change of the mobile phase. By equilibrating the mobile phase early, the timing to inject the next sample is accelerated, and hence both the steps are performed within 30 seconds, preferably 10 seconds. When the solvent injecting device is used, after switching the flow passage switching valve and injecting the solvent, the flow passage switching valve is returned to its original state and operation for equilibrating the mobile phase is performed. Considering a period of time allowing to inject a predetermined solvent, switching operation is preferably performed as quickly as possible.

Both the step of changing the composition of the mobile phase and the step of returning the composition of the mobile phase to the pre-change state according to the present invention are performed during a period of time from detection of the peak which is eluted latest among separation components in the sample to injection of the next sample. Both the steps are performed at this timing, and thus it is possible to promote the extraction of the peak components from the column, and to accelerate the reduction of tailing.

The method of detecting the peaks is not particularly limited. Timing can be calculated by peaks that are detected by a detector ordinarily provided for the supercritical fluid chromatography such as an ultraviolet absorption spectrometer. By generating composition change of the mobile phase at the above-mentioned timing, the effects of the present invention can be exerted. However, when the solvent injecting device is used for the composition change of the mobile phase, the device ordinarily has a dead volume, and hence change of the composition is performed while considering a period of time ($t0$) for causing the mobile phase to pass an outlet of the column after injection of the solvent.

The solvent to be injected by the solvent injecting device is not particularly limited. The same solvent as the solvent contained in the mobile phase may be injected, or a different solvent may be injected. The solvent to be injected may be one kind of solvent, or two more kinds of solvents in the form of mixture. Examples of the kind of the solvent include lower alcohols such as methanol, ethanol, and 2-propanol, a ketone such as acetone, tetrahydrofuran, acetonitrile, ethyl acetate, and water.

Among the above-mentioned solvents, a solvent having a high polarity is preferably used because it further accelerates the reduction of tailing. Further, it is a preferable mode to adopt a solvent having a polarity higher than that of the solvent contained in the mobile phase.

In the method according to the present invention, the step of injecting the sample into the mobile phase can be performed continuously at short intervals. Accordingly, there is preferably adopted a method of separating the target substances through injecting the sample sequentially, that is, performing the above-mentioned three steps sequentially. The intervals to inject the sample at the time of performing such sequential injections of the sample can be set shorter than those of a conventional method. As a result, it is possible to increase the treatment amount of the sample per unit time.

In the present invention, injection of the next sample is performed at a time when the reduction of peak tailing of one of the target substances in the sample is completed. Therefore, the intervals to inject the samples are appropriately determined depending on the target substances.

Supercritical Fluid Chromatography Apparatus According to the Present Invention

The supercritical fluid chromatography apparatus according to the present invention includes a sample injecting device for injecting the sample into the mobile phase, and a solvent injecting device for changing the composition of the mobile phase. In addition, the supercritical fluid chromatography apparatus generally has a column and a mobile phase forming device for forming the mobile phase, which are provided to an ordinary supercritical fluid chromatography apparatus, and has other configurations such as a detector and a pressure regulating device.

The mobile phase forming device is not particularly limited as long as the mobile phase forming device is means capable of forming the mobile phase containing the supercritical fluid and the solvent. The mobile phase forming device can be constituted by, for example, a temperature regulating means, such as a heat exchanger, and a high-pressure pump.

The column is not particularly limited as long as the column has a separating agent capable of separating the target substances in the sample injected into the mobile phase. The separating agent is selected among a variety of separating agents in accordance with the target substances. A mode of the separating agent is not particularly limited. For example, the separating agent may be filled with the column while being carried by a particulate carrier, may be received in the column while being carried by an integrated carrier to be received in the column, or may be received in the column as an integrated molded material formed of the separating agent.

For example, when at least one of the target substances is an optical isomer, a polysaccharide or a polysaccharide derivative having an optical activity is preferably used as the separating agent. Examples of the polysaccharide include cellulose and amylose. Examples of the polysaccharide derivative include a cellulose ester derivative, an amylose ester derivative, a cellulose carbamate derivative, and an amylose carbamate derivative.

The detector is not particularly limited as long as the detector is means capable of detecting the target substances in the mobile phase that passes the column. Examples of the detector include an ultraviolet absorption spectrometer, a differential refractometer, and a polarimetric detector.

The pressure regulating device is not particularly limited as long as the pressure regulating device is means capable of regulating a pressure in the flow passage of the mobile phase ranging from the mobile phase forming device to the detector to a pressure to maintain the mobile phase formed by the mobile phase forming device. For example, a well-known back pressure valve (back pressure regulating valve) can be used as the pressure regulating device.

The supercritical fluid chromatography apparatus according to the present invention may further include another means other than an apparatus for separating the target substances in the sample. Examples of the another means include a taking-out part for taking out the target substances from the mobile phase which passes the pressure regulating device to be released from a supercritical state of the supercritical fluid in the mobile phase, and a gas recovering means for recovering, from the mobile phase released from the supercritical state, components forming the supercritical fluid as gas, and for supplying the components to the mobile phase forming device.

The taking-out part is not particularly limited as long as the taking-out part is a device capable of taking out the target substances from the mobile phase which contains the target substances separated by the column and is released from the supercritical state. Specifically, the taking-out part can be constituted by a vapor-liquid separator such as a cyclone for subjecting, to vapor-liquid separation, the mobile phase released from the supercritical state of the supercritical fluid, a hermetically sealable container which has a lower pressure and receives a separated liquid phase, or the like.

In the present invention, with respect to the pressure regulating device, one taking-out part may be provided, or a plurality of taking-out parts may be provided in parallel. Provision of the plurality of taking-out parts in parallel is preferred in view of taking out a plurality of target substances.

The gas recovering means is not particularly limited as long as the gas recovering means is means capable of recovering, from the mobile phase released from the supercritical state of the supercritical fluid, components forming the supercritical fluid as gas, and of supplying the recovered gas to the mobile phase forming device as a raw material for the supercritical fluid. The gas recovering means can be constituted by, for example, a gas recovering pipe connecting the taking-out part and the mobile phase forming device together, and a recovery vapor-liquid separator for separating the gas and the liquid phase from fluid flowing in the gas recovering pipe.

Examples of the recovery vapor-liquid separator include a cyclone, and a device having, in the flow passage of the gas, an absorbing solution for absorbing the solvent from the recovered gas or a solid absorbent for absorbing the solvent.

When the supercritical fluid chromatography apparatus according to the present invention includes the gas recovering means, it is possible to recycle the recovered gas for formation of the supercritical fluid for the mobile phase. In such a case, when a pressure of the recovered gas to be supplied to the mobile phase forming device is higher than a pressure of fresh gas to be supplied to the mobile phase forming device, the recovered gas is preferably supplied to the mobile phase forming device while higher priority is placed on the recovered gas than on the fresh gas in view of increasing efficiency in recycling of the recovered gas. Such supply of the recovered gas can be performed by, for example, connecting a supply source for the fresh gas with the mobile phase forming device through means such as a regulator for supplying the fresh gas under an appropriate pressure (initial pressure).

In the following, a configuration of the supercritical fluid chromatography apparatus used in an embodiment of the present invention is described.

As illustrated in FIG. 1, the supercritical fluid chromatography apparatus used in this embodiment includes: a gas cylinder 1 filled with carbon dioxide having high pressure; a heat exchanger 2 for cooling carbon dioxide supplied from the gas cylinder 1 to turn the carbon dioxide into a liquefied gas; a high-pressure pump 3 for quantitatively pumping the liquefied gas formed by the heat exchanger 2; a solvent tank 4 for receiving a solvent; a high-pressure pump 5 for quantitatively supplying the solvent from the solvent tank 4 to the liquefied gas pumped by the high-pressure pump 3; and a heat exchanger 6 for heating a mixed fluid containing the liquefied gas and the solvent to turn the liquefied gas in the mixed fluid into a supercritical fluid. The gas cylinder 1 is a supply source for fresh gas. Members ranging from the heat exchanger 2 to the heat exchanger 6 correspond to the mobile phase forming device.

Further, the supercritical fluid chromatography apparatus includes: a sample injecting device 7 for injecting a sample containing target substances (for example, optical isomers) in a formed mobile phase; a column 8 for separating the target substances in the injected sample; a detector 9 for detecting the substances in the mobile phase that pass the column 8; and a back pressure valve 10 for maintaining a pressure in a system ranging from the high-pressure pump 3 to the detector 9 at a predetermined pressure. The back pressure valve 10 corresponds to the pressure regulating device. Note that, a pipe 14 is a pipe for connecting the heat exchanger 6 with the column 8 through an intermediation of the sample injecting device 7. The pipe 14 corresponds to the flow passage of the mobile phase.

Further, the supercritical fluid chromatography apparatus includes: a plurality of vapor-liquid separators 11 each for subjecting, to vapor-liquid separation, the mobile phase which passes the back pressure valve 10; a plurality of first tanks 12 each for receiving a liquid phase separated by each of the vapor-liquid separators 11; and a plurality of second tanks 13 correspondingly connected to the first tanks 12, respectively. Members ranging from the vapor-liquid separators 11 to the second tanks 13 correspond to the taking-out part.

Moreover, the supercritical fluid chromatography apparatus includes: a gas recovering pipe 15 for connecting each of the vapor-liquid separators 11 with the heat exchanger 2; a vapor-liquid separator 16 for separating liquid from recovered gas flowing in the gas recovering pipe 15; a third tank 17 for receiving the liquid phase separated by the vapor-liquid separator 16; and a fourth tank 18 connected to the third tank 17. The vapor-liquid separator 16 corresponds to the recovery vapor-liquid separator. Members ranging from the gas recovering pipe 15 to the fourth tank 18 correspond to the gas recovering means.

In addition, the supercritical fluid chromatography apparatus according to the present invention includes: a regulator 19 for supplying carbon dioxide gas from the gas cylinder 1 at a predetermined pressure; a check valve 20 for preventing a back flow of the gas from the heat exchanger 2 to the gas cylinder 1; a buffer tank 21 for receiving the liquefied gas formed by the heat exchanger 2; two-way valves 22 each provided between the back pressure valve 10 and each of the vapor-liquid separators 11; two-way valves 23 each provided between the first tanks 12 and the second tanks 13, respectively; check valves 26 for preventing a back flow of gas to the vapor-liquid separators 11; and a check valve 27 provided between the third tank 17 and the fourth tank 18.

A solvent injecting device including a solvent tank 30, a high-pressure pump 31, a flow passage switching valve 32, and preferably loop piping 33 is provided for changing composition of the mobile phase of the present invention. The solvent injecting device injects the solvent in the solvent injecting device into the column at specific timing through switching operation for the switching valve 32. Then, immediately after injection of the solvent, the switching valve 32 is switched to return to a state of original flow passage. In order to inject the solvent in a moment through the operation for the switching valve, an inside of the solvent injecting device is maintained at high pressure by the high-pressure pump 31. Provision of the loop piping 33 is preferred because quantitativeness of injection of the sample is improved.

Next, separation of the target substances by the supercritical fluid chromatography apparatus is described.

First, carbon dioxide is supplied from the gas cylinder 1 to the heat exchanger 2 at an appropriate initial pressure. The carbon dioxide cooled by the heat exchanger 2 is turned into the liquefied gas, and is received in the buffer tank 21. The liquefied gas received in the buffer tank 21 is quantitatively pumped by the high-pressure pump 3, and is supplied to the heat exchanger 6 while being pressurized to a predetermined pressure (for example, critical pressure) determined by the back pressure valve 10.

Meanwhile, the solvent (for example, ethanol) is quantitatively pumped by the high-pressure pump 5 from the solvent tank 4 to the liquefied gas. Before supplied to the heat exchanger 6, the solvent joins the liquefied gas to be mixed with the liquefied gas. The mixed fluid containing the liquefied gas and the solvent is supplied to the heat exchanger 6 to be heated to a predetermined temperature (for example, critical temperature or preset temperature of column 8). Owing to this heating, the liquefied gas in the mixed fluid is turned into the supercritical fluid, and the mobile phase containing the supercritical fluid and the solvent is formed.

The sample containing the target substances (for example, optical isomers) is injected into the formed mobile phase from the sample injecting device 7 to the pipe 14.

The mobile phase into which the sample is injected is fed to the column 8 for receiving a separating agent (for example, polysaccharide derivative) selected in accordance with the target substances. In the column 8, the target substances are separated from the sample. The target substances are detected by the detector 9. When the detector 9 detects one of the target substances, any one of the two-way valves 22 is opened, and other two-way valves 22 are closed. The mobile phase containing the target substances is fed to the back pressure valve 10.

Here, the target substances are detected by the detector 9. During a period of time from detection of a peak of one of the target substances which is eluted latest from the column among the target substances to injection of the next sample, the flow passage switching valve 32 of the solvent injecting device is operated, and the pressurized solvent kept in the loop piping 33 is injected into the column in a moment. After injection of the solvent, the switching valve 32 is switched to return the flow passage to the ordinal flow passage of the mobile phase.

Then, after tailing of the detected peak is reduced, the sample is reinjected from the sample injecting device 7 to the pipe 14. Controls of the switching valve 32 and the sample injecting device 7 can be also automatically performed at constant intervals by a control system that is separately provided.

The mobile phase that passes the back pressure valve 10 is released from pressure regulation performed by the back pressure valve 10, is decompressed, and is supplied to predetermined one of the vapor-liquid separators 11. The mobile phase fed to the predetermined one of the vapor-liquid separators 11 is subjected to vapor-liquid separation. The carbon dioxide forming the supercritical fluid is separated as a gas phase, and the target substances and the solvent are separated as the liquid phase. The liquid phase is received in one of the first tanks 12, and is further received in one of the second tanks 13 having low pressure. The liquid phase received in the second tank 13 is taken out from the second tank 13. The solvent and the target substances are separated from the liquid phase by a well-known method such as vacuum concentration and vacuum distillation, and the target substances can be obtained. The solvent may be purified as needed and be recycled as the mobile phase.

The carbon dioxide separated by the predetermined one of the vapor-liquid separators 11 is fed to the vapor-liquid separator 16 through an intermediation of one of the check valves 26.

When one of the target substances other than the detected target substance is detected by the detector 9, one of the two-way valves 22 corresponding to the predetermined one of the vapor-liquid separators 11 for the detected target substance is closed. Then, another one of the two-way valves 22 corresponding to another one of the vapor-liquid separators 11 is opened, and the mobile phase containing one of the target substances other than the detected target substance is similarly subjected to vapor-liquid separation by another one of the vapor-liquid separators 11.

The carbon dioxide (recovered gas) fed to the vapor-liquid separator 16 is subjected to vapor-liquid separation by the vapor-liquid separator 16. A micro amount of liquid phase (solvent) contained in the recovered gas is received in the third tank 17, and then received in the fourth tank 18 to be discarded.

The recovered gas purified by the vapor-liquid separator 16 is fed to the heat exchanger 2 through the gas recovering pipe 15. When a pressure of the recovered gas is higher than the initial pressure determined by the regulator 19, the recovered gas is supplied to the heat exchanger 2 and is liquefied. When the pressure of the recovered gas is lower than the initial pressure determined by the regulator 19, fresh carbon dioxide gas is supplied from the gas cylinder 1 to the heat exchanger 2 and is liquefied.

Note that, in this embodiment, by connecting the second tanks 13 and the vapor-liquid separator 16 with each other by pipes, it is possible to further recover the carbon dioxide discharged from the liquid phase in the second tanks 13. With this configuration, a recovery rate of gas to be used as a raw material for the supercritical fluid is increased, and such a configuration is further effective particularly in view of reducing manufacturing cost of the target substances.

EXAMPLES

In the following, the effects of the present invention are described in detail with reference to Examples. However, the present invention is not limited to Examples described below.

Example 1

With use of the supercritical fluid chromatography apparatus illustrated in FIG. 1, flurbiprofen was separated from a sample containing the flurbiprofen under the following conditions.

When 6.4 minutes elapsed after injection of the sample containing flurbiprofen, 100 μL of ethanol was injected in a moment through switching of a switching valve, and the valve was returned to its original state. In this case, the apparatus had a dead volume, and hence the ethanol was eluted when 7.3 minutes elapsed.

Figure 3:
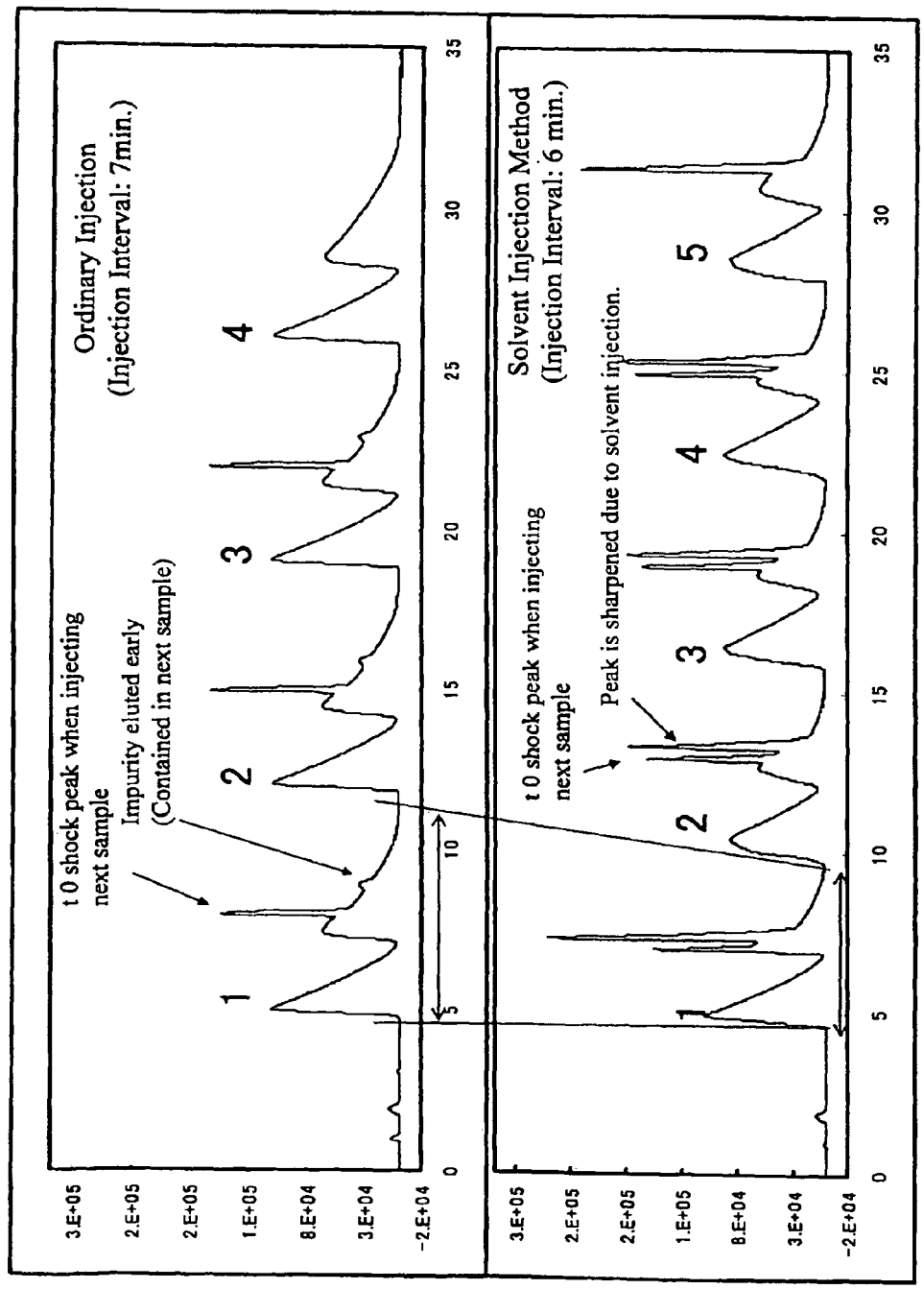
FIG. 3 is a graph showing comparison of peaks between a method of Example 1 and an ordinary injecting method.

Owing to injection of the ethanol, peak components were suddenly extracted, and hence peaks were sharpened and a reduction of tailing was accelerated by 1 minute. States of the peaks are shown in FIG. 2 and FIG. 3.

Column: CHIRALPAK AD-H (0.46×25 cm) manufactured by DAICEL CHEMICAL INDUSTRIES, LTD.
Mobile phase: $CO_2$/EtOH=95/5
Flow rate of mobile phase: 4 mL/min
Temperature: 25° C.
Pressure: 10 MPa
Detection: 290 nm
Sample: 40 μL of ethanol solution containing flurbiprofen (250 mg/mL in EtOH)
Injected solvent: EtOH
Injection amount of solvent: 100 μL

Example 2-(1)

Similarly to Example 1, with use of the supercritical fluid chromatography apparatus illustrated in FIG. 1, benzoin ethyl ether was separated from a sample containing the benzoin ethyl ether under the following conditions.

When 3.2 minutes elapsed after injection of the sample containing benzoin ethyl ether, 300 μL of tetrahydrofuran (THF) was injected in a moment through switching of a switching valve, and the valve was returned to its original state. In this case, the apparatus had a dead volume, and hence the THF was eluted when 4.1 minutes elapsed.

Figure 4:
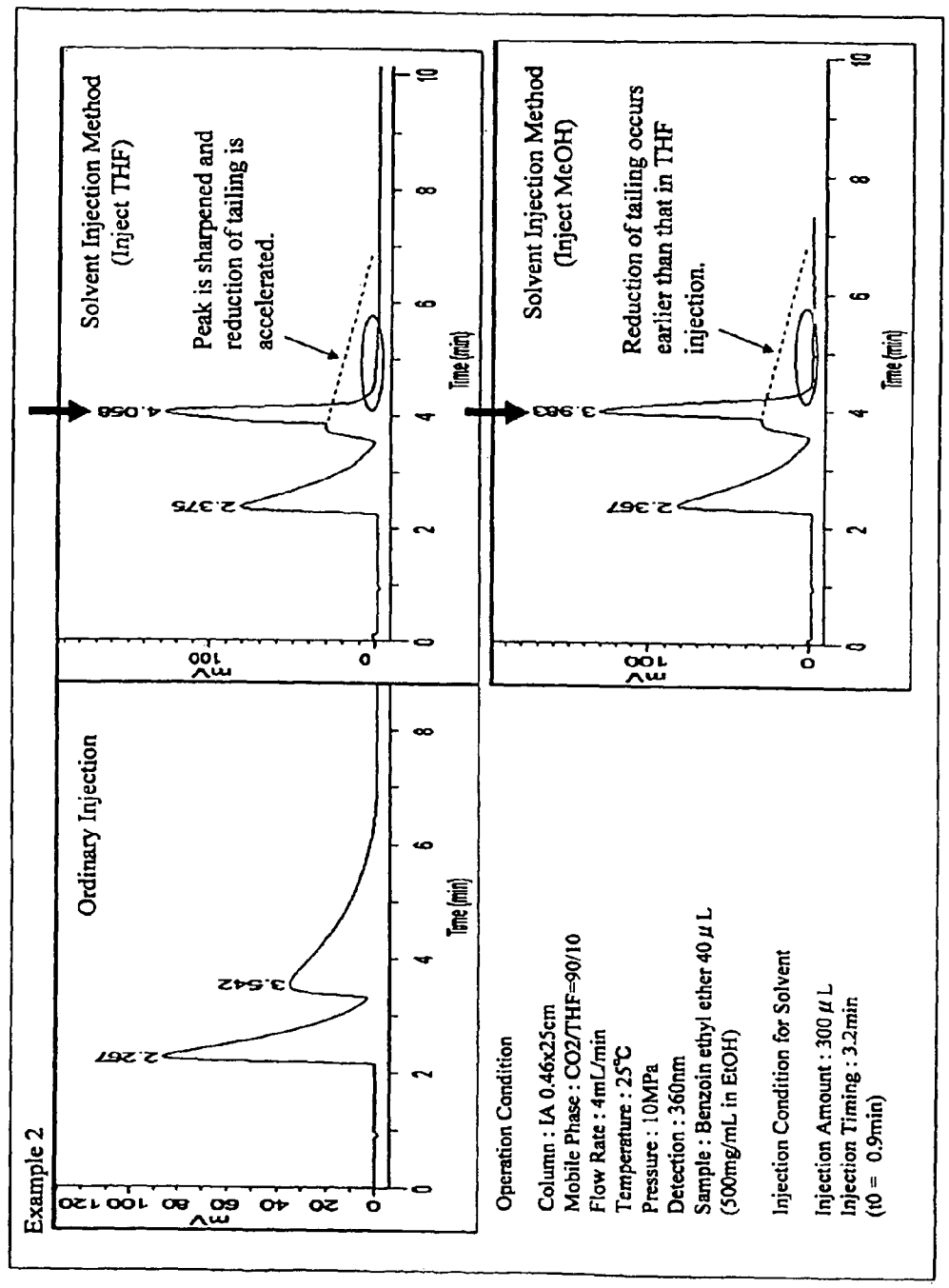
FIG. 4 is a graph showing a reduction of peak tailing according to Example 2.
Figure 5:
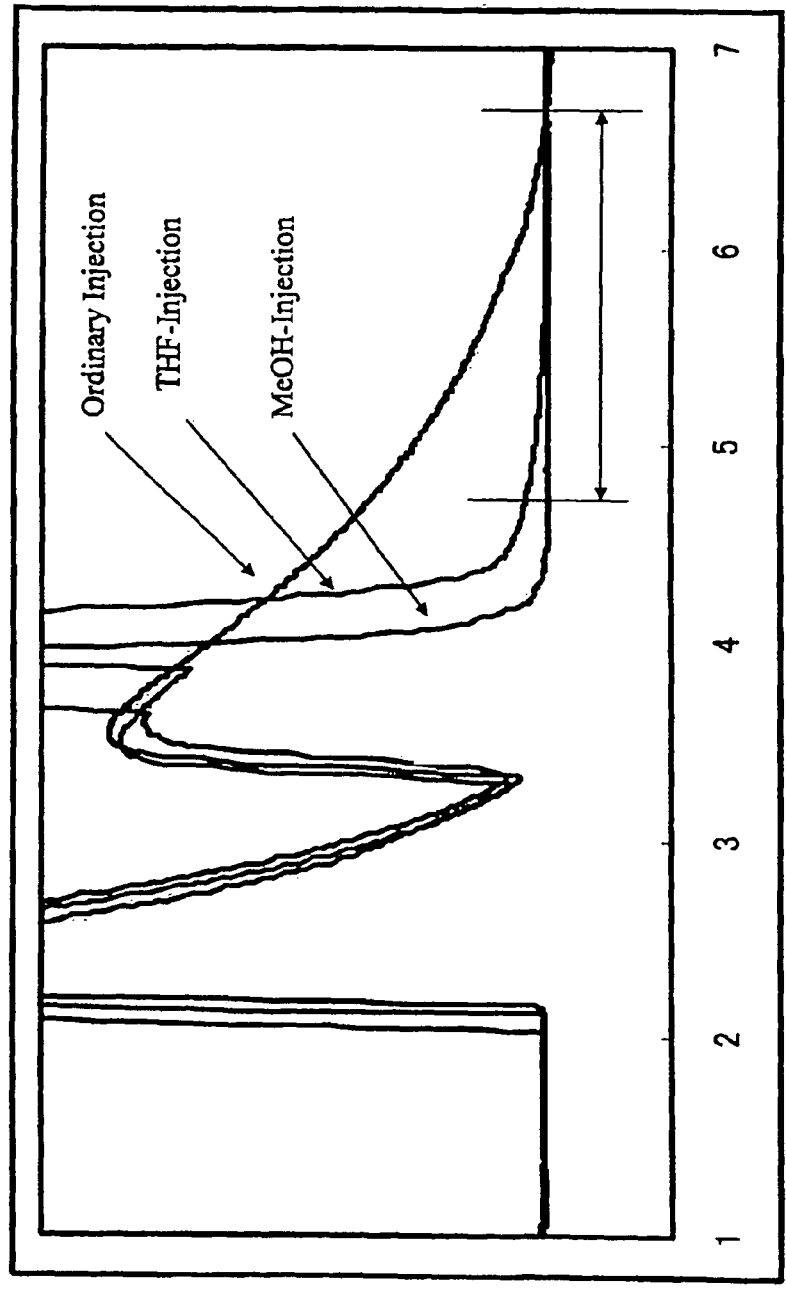
FIG. 5 is an enlarged graph showing the reduction of peak tailing according to Example 2.

Owing to injection of the THF, peak components were suddenly extracted, and hence peaks were sharpened and a reduction of tailing was accelerated by 1 minute. States of the peaks are shown in FIG. 4 and FIG. 5.

Column: CHIRALPAK IA (0.46×25 cm) manufactured by DAICEL CHEMICAL INDUSTRIES, LTD.
Mobile phase: $CO_2$/THF=90/10
Flow rate of mobile phase: 4 mL/min
Temperature: 25° C.
Pressure: 10 MPa
Detection: 360 nm
Sample: 40 μL of ethanol solution containing benzoin ethyl ether (500 mg/mL in EtOH)
Injected solvent: THF
Injection amount of solvent: 300 μL

Example 2-(2)

Similarly to Example 2-(1) except that the THF was replaced by methanol as the injected solvent, benzoin ethyl ether was separated from a sample containing the benzoin ethyl ether.

Owing to injection of the methanol, peak components were suddenly extracted, and hence peaks were sharpened and a reduction of tailing was accelerated by 2 minutes. States of the peaks are shown in FIG. 4 and FIG. 5.

Reference Example 1

A method of changing the composition of the mobile phase according to the present invention was applied to high performance liquid chromatography (HPLC), and trans-stilbene oxide (t-SO) was separated from a sample containing the t-SO under the following conditions.

When 5.8 minutes elapsed after injection of the sample containing t-SO, 30 μL of n-hexane/2-propanol (IPA) was injected in a moment through switching of a switching valve, and the valve was returned to its original state. In this case, the apparatus had a dead volume, and hence the THF was eluted when 13.5 minutes elapsed.

Figure 6:
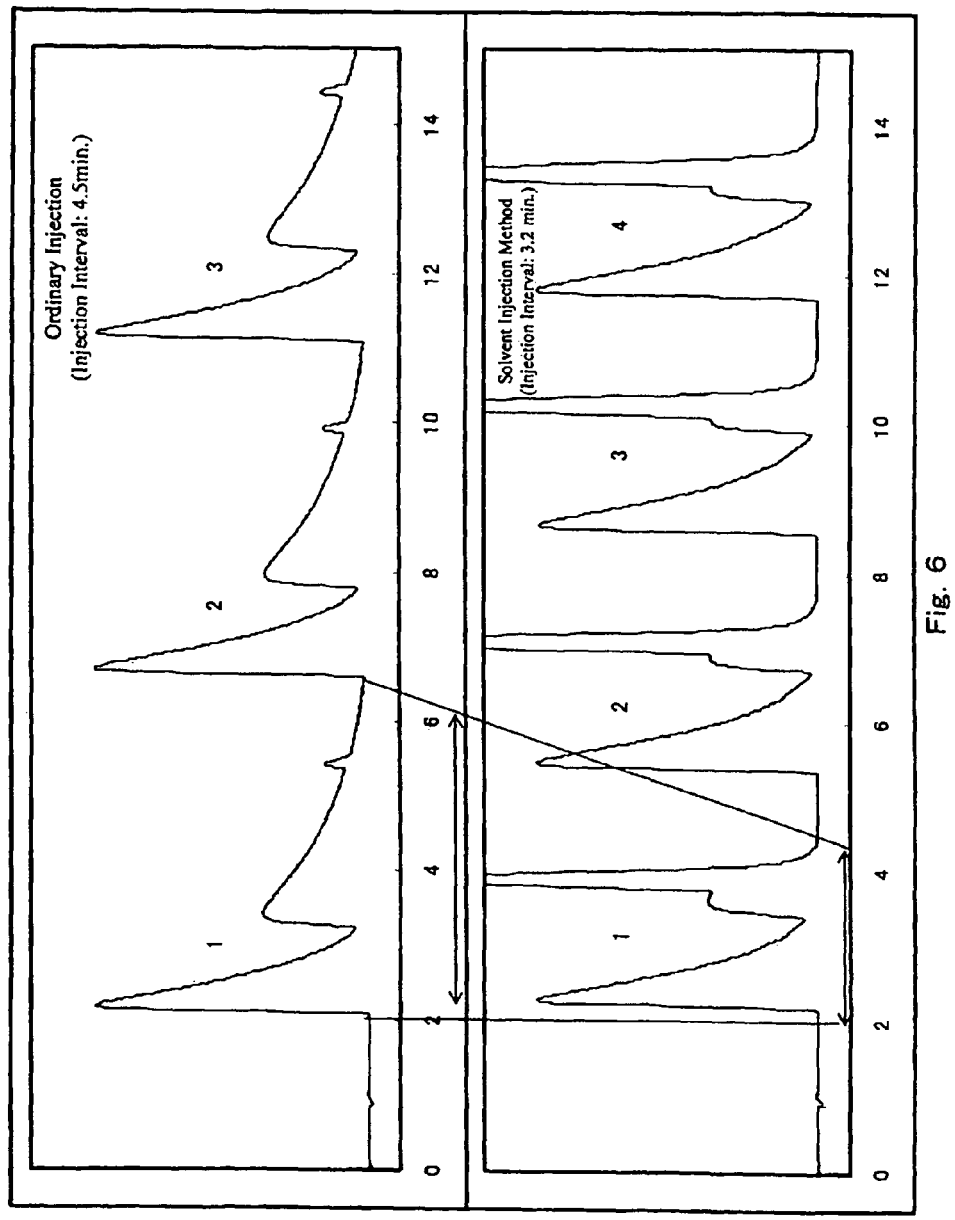
FIG. 6 is a graph showing comparison of peaks between a method of Example 2-(2) and the ordinary injecting method.
Figure 7:
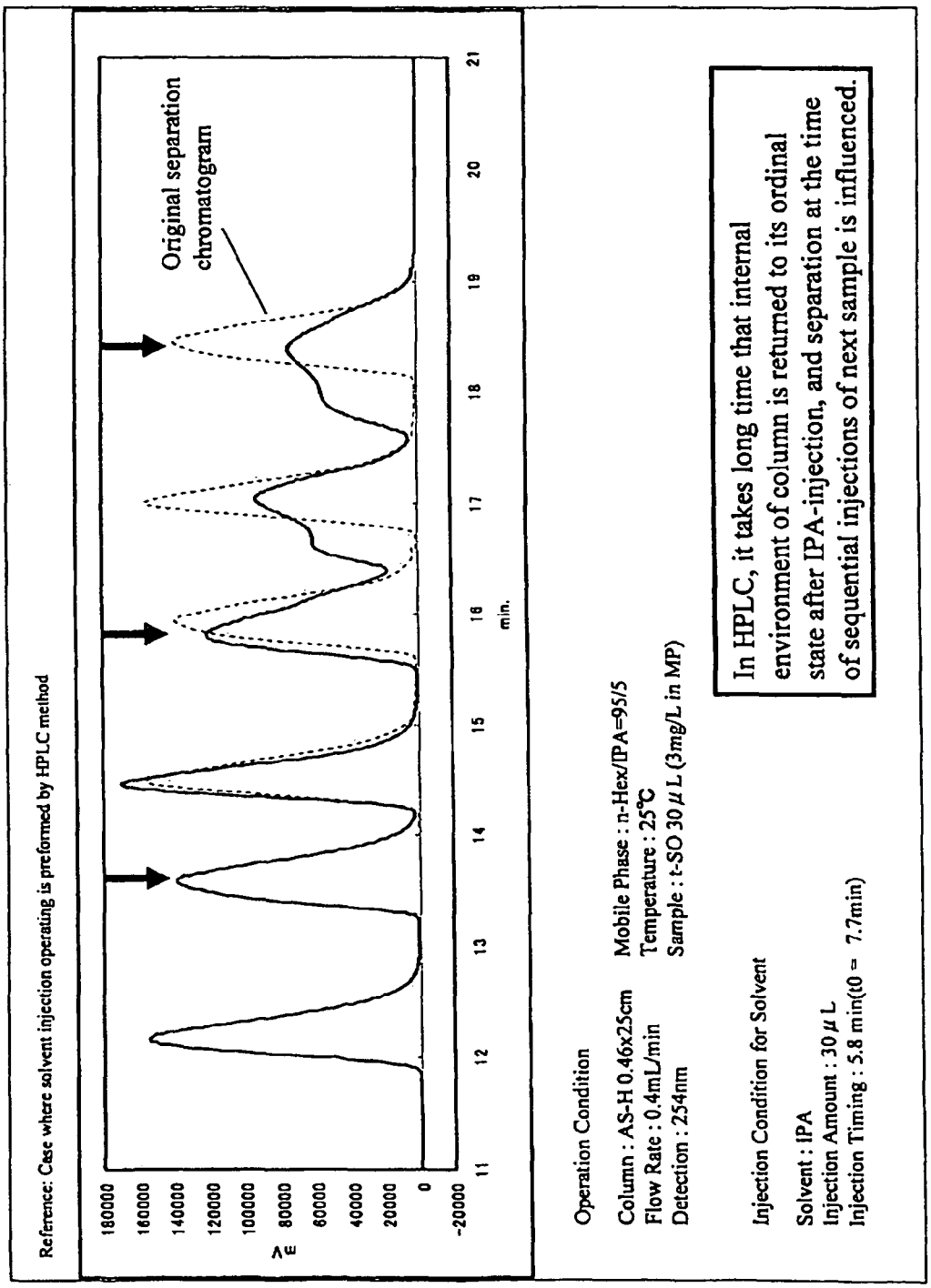
FIG. 7 is a graph showing peaks according to Reference Example.

In HPLC, it takes long time that internal environment of the column is returned to its original state after injection of IPA, and separation at the time of sequential injections of next sample is influenced. States of peaks are shown in FIG. 6.

Column: CHIRALPAK AS-H (0.46×25 cm) manufactured by DAICEL CHEMICAL INDUSTRIES, LTD.
Mobile phase: n-hexane/IPA=95/5
Flow rate of mobile phase: 0.4 mL/min
Temperature: 25° C.
Pressure: normal pressure
Detection: 254 nm
Sample: 30 μL of MP solution containing t-SO (3 mg/mL in MP)
Injected solvent: IPA
Injection amount of solvent: 30 μL

DESCRIPTION OF REFERENCE NUMERALS

1 gas cylinder
2, 6 heat exchanger
3, 5, 31 high-pressure pump
4, 30 solvent tank
7 sample injecting device
8 column
9 detector 10 back pressure valve
11, 16 vapor-liquid separator
12 first tank
13 second tank
14 pipe
15 gas recovering pipe
17 third tank
18 fourth tank
19 regulator
20, 26 check valve
21 buffer tank
22, 23 two-way valve
32 switching valve
33 loop piping

The invention claimed is:

1. A method of manufacturing target substances by, with use of a supercritical fluid chromatography apparatus, separating the target substances from a sample injected into a mobile phase containing a supercritical fluid and a solvent, the method comprising the steps of:
  injecting the sample into the mobile phase;
  changing a composition of the mobile phase after injecting the sample into the mobile phase; and
  returning the composition of the mobile phase to a pre-change state after changing the composition of the mobile phase,
  wherein the step of changing the composition of the mobile phase and the step of returning the composition of the mobile phase to the pre-change state are performed during a period of time from detection of a peak of one of the target substances which is eluted latest from a column among the target substances separated by the supercritical fluid chromatography apparatus to injection of the next sample.

2. A method according to claim 1, wherein the step of changing the composition of the mobile phase is performed by injecting solvent.

3. A method according to claim 2, wherein the solvent is injected by an amount equal to or more than an injecting volume of the sample and equal to or less than thirty times the injecting volume of the sample.

4. A method according to claim 2, wherein as the solvent to be injected in the step of changing the composition of the mobile phase, a solvent having a polarity higher than a polarity of the solvent contained in the mobile phase is used.

* * * * *